US00PP30618P2

(12) United States Plant Patent
Hansen

(10) Patent No.: US PP30,618 P2
(45) Date of Patent: Jun. 25, 2019

(54) ***HEUCHERA* PLANT NAMED 'TWIST OF LIME'**

(50) Latin Name: ***Heuchera* hybrid**
Varietal Denomination: Twist of Lime

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 15/932,170

(22) Filed: Feb. 14, 2018

(51) Int. Cl.
*A01H 5/12* (2018.01)
*A01H 6/80* (2018.01)

(52) U.S. Cl.
USPC ..... Plt./440

(58) Field of Classification Search
USPC ..... Plt./440
CPC ... A01H 5/02; A01H 5/12; A01H 5/00; A01H 5/025; A01H 6/80
See application file for complete search history.

(56) References Cited

U.S. PATENT DOCUMENTS

PP29,361 P2 * 6/2018 Hansen ..... A01H 6/80
Plt./440

OTHER PUBLICATIONS

Germania Seed Company Walters Gardens Bare Root and Plug Perennials Program #49 2017, retrieved on Jan. 28, 2019, retrieved from the Internet at https://www.germaniaseed.com/pdf/2018/749_walters.pdf, pp. 1, 12, 22. (Year: 2017).*

Walters Gardens *Heuchera* 'Twist of Lime' retrieved on Jan. 28, 2019, retrieved from the Internet at https://www.waltersgardens.com/variety.php?ID=HEUTL, one page. (Year: 2019).*

* cited by examiner

*Primary Examiner* — June Hwu

(57) ABSTRACT

The new and distinct hybrid of *Heuchera* plant named 'Twist of Lime' with cordate foliage of bright yellowish lime green in summer, slightly cupped and with a crisped mucronulate margin. The new plant has chartreuse calyces that develop reddish tint along with the reddish styles on older flowers. The new plant is vigorous, and produces dense compact clumps and is useful in the landscape or in containers.

1 Drawing Sheet

Botanical denomination: *Heuchera* hybrid.
Variety denomination: 'Twist of Lime'.

BACKGROUND OF THE INVENTION

The present invention relates to a new and distinct cultivar of Coral Bells in the Saxifragaceae family and given the cultivar name of 'Twist of Lime'. *Heuchera* 'Twist of Lime' was hybridized by the inventor on Mar. 15, 2013 at a wholesale perennial nursery in Zeeland, Mich., USA and assigned the breeder code 13-414-17 through trials at the same nursery. The seed or female parent was a propriety unreleased hybrid known by the breeder code 12-115-02 (not patented) and the pollen or male parent was a proprietary selection from a commercial seed line known as *Heuchera americana* 'Malachite' (not patented) and given the breeder code "one."

*Heuchera* 'Twist of Lime' was first selected in the fall of 2014 and passed final evaluation in the fall of 2015 from among thousands of other seedlings from the same cross and hundreds of other crosses. *Heuchera* 'Twist of Lime' has been asexually propagated by division at the same nursery in Zeeland, Mich. since 2015 and by careful shoot tip tissue culture propagation and the resultant plants have remained stable and continued to exhibit the same characteristics as the original plant for multiple generations.

No plants of *Heuchera* 'Twist of Lime' have been sold, in this country or anywhere in the world, prior to the filing of this application, nor has any disclosure of the new plant been made prior to the filing of this application except that which was disclosed within one year of the filing of this application, and was either derived directly or indirectly from the inventor.

BRIEF SUMMARY OF THE INVENTION

Compared with the male parent, *Heuchera* 'Twist of Lime' has chartreuse to yellow foliage, depending on light intensity, and the flowers are more chartreuse with accents of red compared with the creamy flowers and medium green, highly crisped foliage of the male parent. The female parent has flatter, more bronze-colored and larger leaves than the new plant. Further comparison with the female parent is not possible as neither the plant nor photographs of the female parent have been maintained. The nearest comparison coral bell cultivars are 'Pear Crisp' U.S. Plant Pat. No. 23,568 which is more dissected, has less crisped foliage of a chartreuse with flowers of creamy white; 'Pretty Pistachio' U.S. Plant Pat. No. 29,361 which has larger leaves that are less undulate and crisped and have brighter yellow coloring and flowers and calyxes of pink; 'Citronelle' U.S. Plant Pat. No. 17,934 has much flatter leaves with no crisping and larger cream-colored flowers.

*Heuchera* 'Twist of Lime' differs from its parents as well as all other coral bells known to the applicant in the following combined traits:

1. The cordate leaf blades are bright yellowish-lime in mid-season.

2. Leaf shape is cordate, frequently slightly cupped with crisped and mucronulate.
3. Upright panicles produce tiny flowers with chartreuse calyx bases tipped with reddish styles and sepal apices and small near white petals.
4. Plant is vigorous and produces dense, compact foliage.

BRIEF DESCRIPTION OF THE DRAWINGS

The photographs of the new plant demonstrate the overall appearance of the plant including the unique traits. The colors are as accurate as reasonably possible with modern color reproductions. Some slight variation of color may occur as a result of lighting quality, intensity, wavelength, and direction or reflection.

DETAILED BOTANICAL DESCRIPTION

Figure 1:
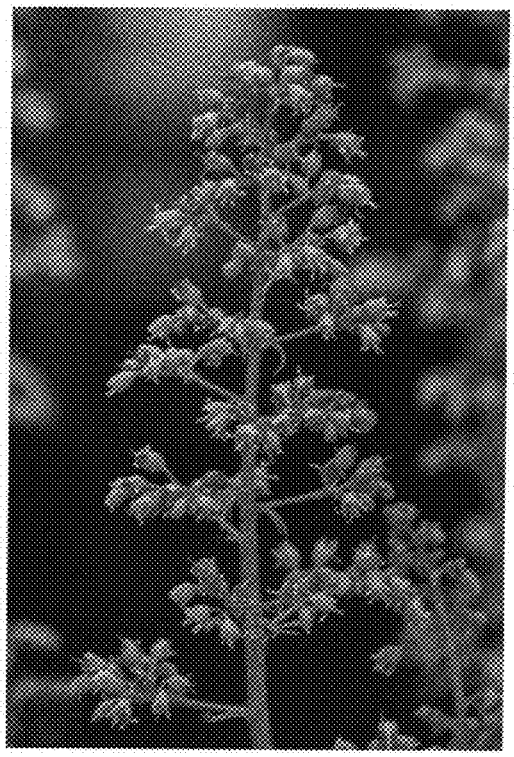
FIG. 1 shows a close-up of the flowers and buds.
Figure 2:
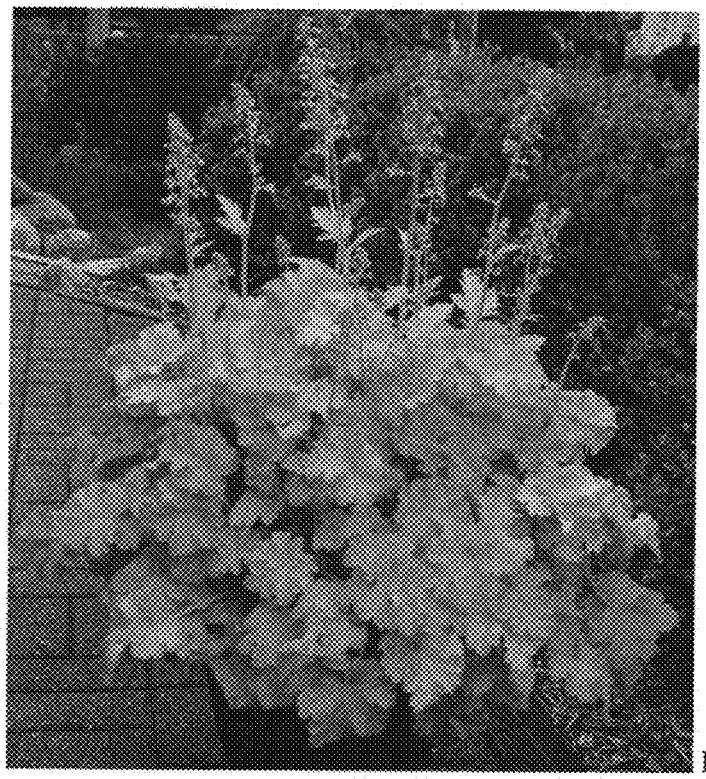
FIG. 2 shows a two-year-old plant in full flower.

The following description is based on a two-year-old plant growing in a lightly shaded greenhouse in Zeeland, Mich., USA. The new plant has not been grown under all possible environments and may phenotypically appear different under different conditions such as light, temperatures, fertilizer, and water, without any difference in genotype. The color descriptions used are from the 2015 edition of The Royal Horticultural Society Colour Chart except where common dictionary terms are used.

Parentage: The female or seed parent is a propriety unreleased hybrid known by the breeder code 12-115-02 (not patented) comprised of a cross between 'Mocha' U.S. Plant Pat. No. 18,386 and a proprietary selection of *Heuchera rubescens*, and the pollen or male parent was a single seedling proprietary selection from a commercial seed line known as *Heuchera americana* 'Malachite' and given the breeder code "one" (not patented) to distinguish from other seedlings;

Plant habit: Hardy herbaceous perennial with basal rosette of foliage; mounded foliage to about 25 cm tall and 40 cm in diameter with scapes to about 50 cm long; stems to about 4.0 cm long and 1.0 cm diameter at base with about 10 to 14 leaves per stem and six main stems per plant;

Roots: Fibrous, finely branched;

Growth rate: Rapid, rooting from cutting in two weeks and finishing in three-liter container in about 3 months;

Foliage: Cordate, minutely puberulent adaxial and abaxial; palmately lobed with five main lobes dissected about one-third the way to petiole, medium indentations; apex and lobes acute and mucronulate, base cordate to auriculate with basal lobes frequently overlapping; margins dentate to mucronate, ciliolate; glossiness absent, matte adaxial and abaxial; held nearly horizontal; marginal undulation strong and crisped;

Leaf blade size: To about 8.0 cm wide and 8.5 cm long, average about 7.5 cm wide and 8.0 cm long;

Leaf color: Spring and young emerging leaves adaxial variable with some regions in higher light nearest blend of between RHS 2B and RHS 151D and others more chartreuse nearest RHS N144C with no silver or dark green marbling surrounding the veins, spring young emerging leaves abaxial variable with some regions nearest blend between RHS 151A and RHS 2B and other regions nearest RHS 145C; mature mid-season leaves adaxial variable depending on light exposure with some leaves nearest blend between RHS 145A and RHS N144A and others nearest blend of between RHS 2B and RHS 151D with some leaves developing a thin region surrounding the veins or nearest RHS 174B, abaxial mature mid-season leaves nearest RHS 145C; mid-winter adaxial color variable with distal portion a mixture of nearest RHS 177A and a blend of RHS 182B and RHS 177B, toward petiole nearest RHS 139B; mid-winter abaxial nearest blend between RHS 147C and RHS 147D proximally and nearest RHS 147D with light undertone of nearest RHS 183A;

Leaf quantity: Dense, about 180 per plant;

Veins: Palmate, sparsely hirsutulous adaxial and puberulent abaxial; costate abaxial and nearly flat adaxial;

Vein color: On emerging or early spring foliage adaxial blend nearest RHS 145C with emerging or early spring abaxial nearest RHS 145C; mid-season and flowering time adaxial nearest RHS 160D, mid-season and flowering time abaxial between RHS 145C and RHS 145D; winter adaxial veins proximally nearest RHS 199D distally same as surrounding tissue, and abaxial veins nearest RHS 148D;

Petiole: Terete, with base amplexicaul; with pubescent hairs to about 2.0 mm long; average about 14.0 cm long and about 3.5 mm diameter at base; with stipule;

Petiole color: Emerging leaf nearest RHS 145C; mature leaf nearest RHS 146D;

Stipule: At base of petiole, about 14.0 mm long and about 12.0 mm wide at base; with two acute apical lobes;

Stipule color: Adaxial and abaxial marginal portion nearest RHS 145D with adaxial and abaxial longitudinal middle nearest RHS 145C;

Peduncle: Highly branched panicle; terete; stiff; pubescent; upright; to about 50.0 cm long and 4.5 mm diameter at base, average about 48.0 cm tall and about 4.0 mm diameter; flowering in upper 16 cm; about twenty per plant with up to about 160 flowers per panicle, average about 130; heavily-branched panicle with about 18 branches per peduncle up to about 4.5 cm long and about 1.0 mm diameter at base, decreasing distally; branches mostly outwardly; flower density moderate;

Flowering longevity: Panicle effective for about four weeks;

Peduncle color: Blend between RHS 146D and RHS 153A;

Peduncle bracts: Subtending branches; bifid; acute apex; truncate base; drooping; ciliolate dentate margin; color nearest RHS 153A abaxial and adaxial;

Pedicel: Terete, finely puberulent, average about 2.5 mm long and 0.7 mm diameter;

Pedicel color: Blend between RHS 146D and RHS 153A;

Buds one day prior to opening: Ellipsoidal; rounded apex and attenuate base; puberulent to glandular; about 5.0 mm long and 2.5 mm diameter;

Bud color one day prior to opening: Nearest RHS 153A;

Flower: Perfect, campanulate, actinomorphic, about 6.5 mm long and 8.5 mm in diameter at face; individual flowers lasting about 4 days on plant or as cut flower; persistent;

Flower attitude: Mostly outwardly to slightly drooping;

Calyx: Five, apex acute, base fused in proximal 3.5 mm to form hypanthium; pubescent abaxial, glabrous adaxial; about 6.0 mm long and 4.5 mm wide; persistent;

Sepal color: Young flowers abaxial nearest RHS 151D, adaxial nearest RHS 151B; mature flower developing strong blush of nearest RHS 185B in distal adaxial sepals;

Petals: Five; oblanceolate to spatulate; acute apex and attenuate base; margin entire, glabrous abaxial and adaxial; about 4.0 mm long and 1.5 mm wide at middle;

Petal color: Abaxial and adaxial nearest RHS NN155D;

Androecium: Five adnate to adaxial calyx;

*Filaments*.—Five, thin, glabrous; about 3.0 mm long and less than 0.3 mm diameter; color nearest RHS NN155D.

*Anthers*.—Not observed.

*Pollen*.—Not observed.

Gynoecium: One, two-beaked; half-inferior; bifid style with pistil split at ovary; 6.0 mm long;

*Style*.—Bifid; split apart at apex of ovary; about 4.5 mm long and about 1.0 mm diameter; color beginning nearest RHS N155B developing to nearest RHS 187C in mature flowers.

*Stigma*.—Acute apex, about 0.1 mm diameter; initial color nearest RHS NN155D developing to nearest RHS 187C.

*Ovary*.—Half-inferior, about 2.5 mm long and 2.0 mm diameter; ellipsoidal to globose, base rounded; color nearest RHS 150D.

Fruit: Two-beaked ellipsoidal capsule; about 3.0 mm long and 1.7 mm across; color nearest RHS 200B;

Seed: Thin ellipsoidal; less than 1.0 mm long and less than 0.5 mm wide; color between RHS 202A and RHS 200A;

Disease and pest tolerance: The new plant grows best with ample moisture and drainage in either sun or shade. Cold hardy from USDA zones 4 to 9. Other resistance and tolerance outside of that normal for coral bells is not known.

It is claimed:

1. The new and distinct coral bells plant named *Heuchera* 'Twist of Lime' as herein described and illustrated.

* * * * *